US011678978B2

(12) United States Patent
Hangya et al.

(10) Patent No.: US 11,678,978 B2
(45) Date of Patent: Jun. 20, 2023

(54) LENS CASE AND LENS DELIVERY SYSTEM

(71) Applicant: MEDICONTUR MEDICAL ENGINEERING LIMITED, Zsambek (HU)

(72) Inventors: Peter Hangya, Bicske (HU); Laszlo Kontur, Budapest (HU)

(73) Assignee: MEDICONTUR MEDICAL ENGINEERING LIMITED, Zsambek (HU)

( * ) Notice: Subject to any disclaimer, the term of this patent is extended or adjusted under 35 U.S.C. 154(b) by 279 days.

(21) Appl. No.: 16/958,274

(22) PCT Filed: Dec. 28, 2018

(86) PCT No.: PCT/HU2018/050055
§ 371 (c)(1),
(2) Date: Jun. 26, 2020

(87) PCT Pub. No.: WO2019/130032
PCT Pub. Date: Jul. 4, 2019

(65) Prior Publication Data
US 2020/0345482 A1      Nov. 5, 2020

(30) Foreign Application Priority Data

Dec. 28, 2017  (WO) ................ PCT/HU2017/000054

(51) Int. Cl.
*A61F 2/16*           (2006.01)
(52) U.S. Cl.
CPC .......... *A61F 2/1691* (2013.01); *A61F 2/1678* (2013.01); *A61F 2002/1689* (2013.01); *A61F 2250/0037* (2013.01)

(58) Field of Classification Search
CPC .................. A61F 2/1691; A61F 2/1678; A61F 2002/1683; A61F 2002/1689;
(Continued)

(56) References Cited

U.S. PATENT DOCUMENTS 7,156,854 B2 * 1/2007 Brown .................. A61F 2/1678
623/6.11
2005/0049606 A1   3/2005 Vaquero et al.
(Continued)

FOREIGN PATENT DOCUMENTS

| EP | 1114623 B1 | 5/2008 |
|----|-----------|--------|
| WO | 20050084588 A1 | 9/2005 |
| WO | 20130038021 A1 | 3/2013 |

*Primary Examiner* — Paul B Prebilic
(74) *Attorney, Agent, or Firm* — Olson & Cepuritis, Ltd.

(57) ABSTRACT

The invention relates to a lens case (50, 150) for accommodating an intraocular lens, IOL (1). The lens case (50, 150) comprises a lens case body (3, 103) and a sliding element (4, 104) which can slide on the lens case body from a first position to a second position. The lens case body (3, 103) comprises a longitudinal recess (32, 132), having a first part (32a, 132a) and a second part (32b, 132b), the first part (32a, 132a) being adapted to receive a side zone of the IOL (1) comprising at least one haptic (2), the second part (32b, 132b) being adapted to receive a narrower central zone of the IOL (1). The sliding element (4, 104) comprises a bolt (5, 105a) arranged adjacent a loading port (34, 134) of the second part (32b, 132b) of the recess (32, 132) for displacing the IOL (1) within the recess (32, 132).

19 Claims, 16 Drawing Sheets

(58) Field of Classification Search
CPC .. A61F 2002/16901; A61F 2002/16905; A61F 2250/0037; A61F 2250/001; A61F 2250/0039
See application file for complete search history.

(56) References Cited

U.S. PATENT DOCUMENTS

| | | |
|---|---|---|
| 2010/0036385 A1 | 2/2010 | Isaacs et al. |
| 2011/0112637 A1* | 5/2011 | Kontur ............... A61F 2/16 623/6.43 |
| 2013/0066422 A1* | 3/2013 | Dworschak ......... A61F 2/1613 623/6.51 |
| 2015/0045805 A1* | 2/2015 | Kontur ............... A61F 2/1678 606/107 |
| 2021/0059811 A1* | 3/2021 | Hangya .............. A61F 2/1691 |

* cited by examiner

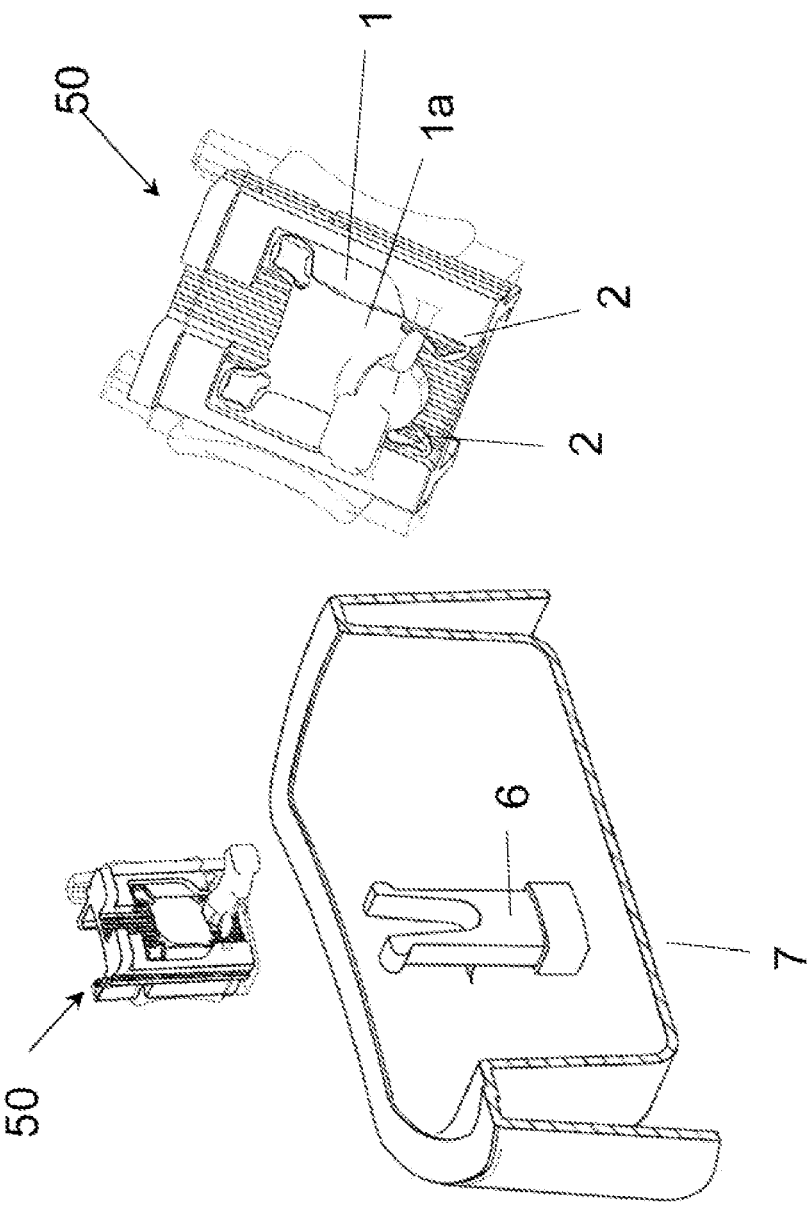

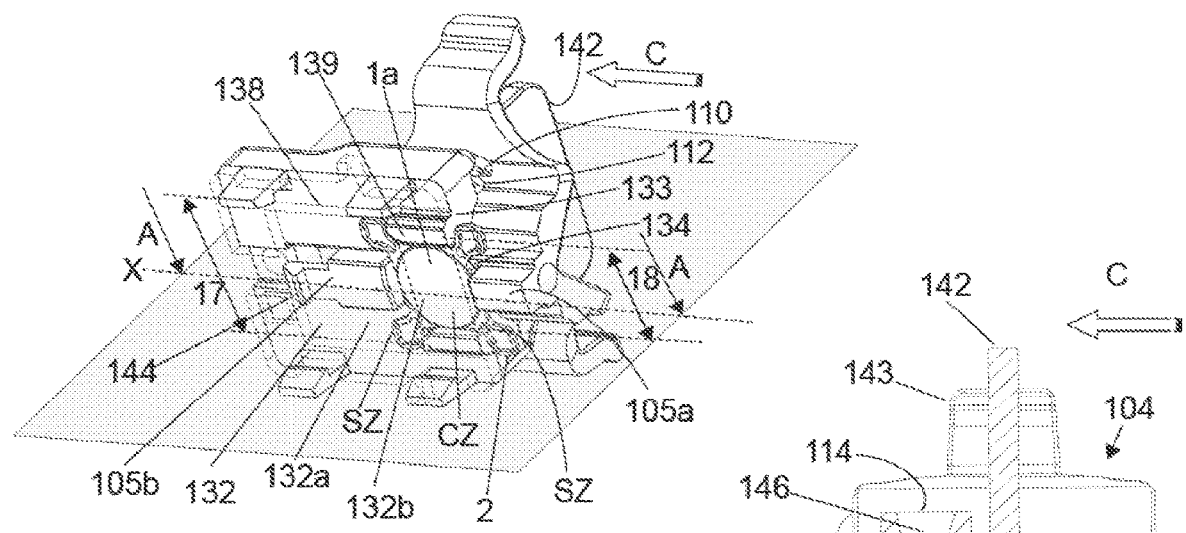
Figure 13A
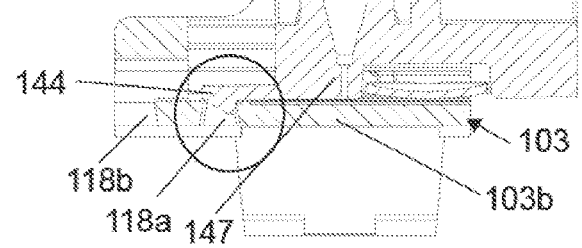
Figure 13.1A
A-A
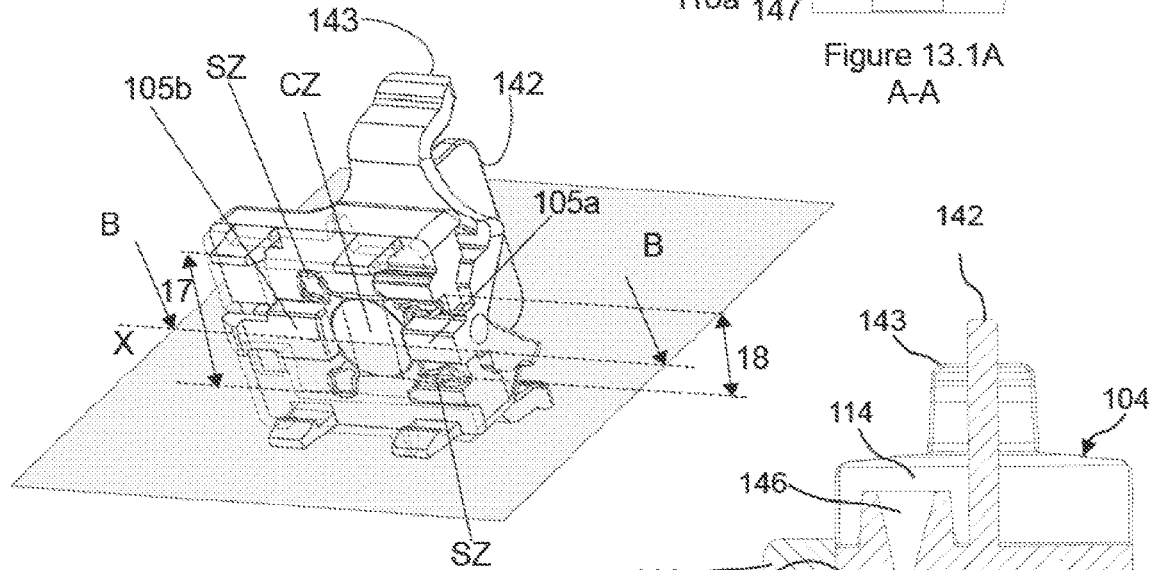
Figure 13B
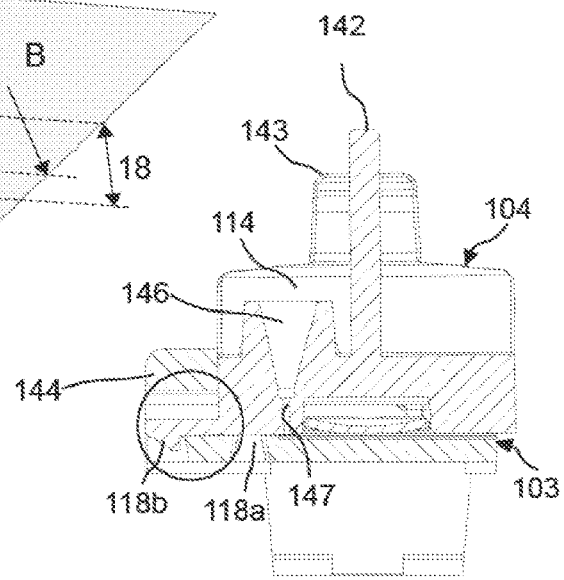
Figure 13.1B
B-B

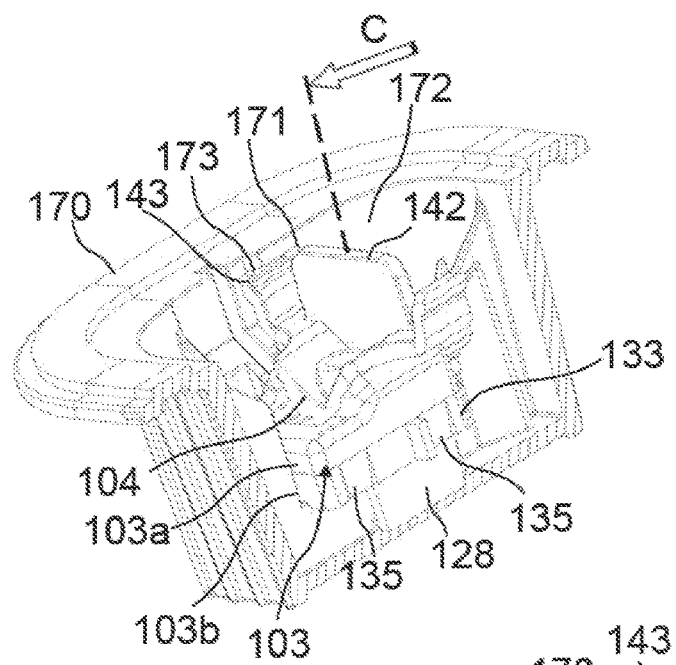
Figure 14A
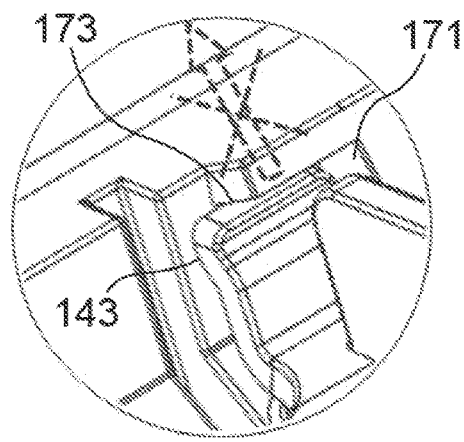
Figure 14.1A
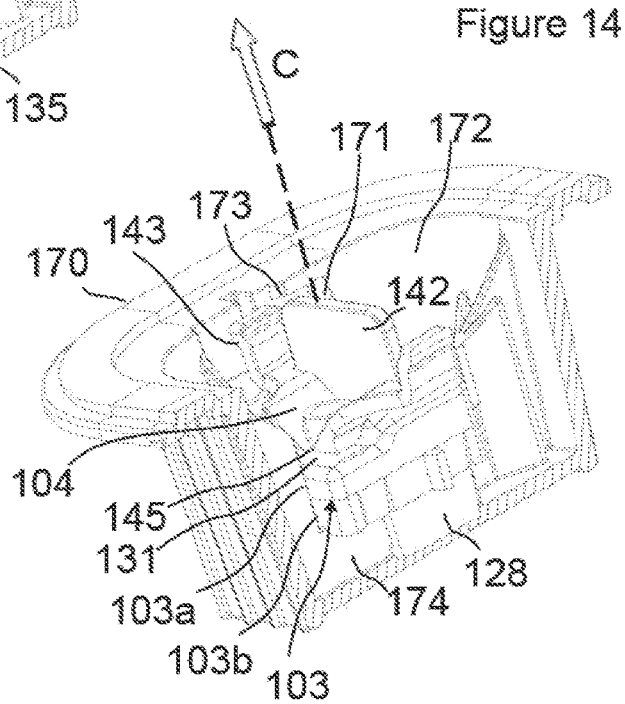
Figure 14B

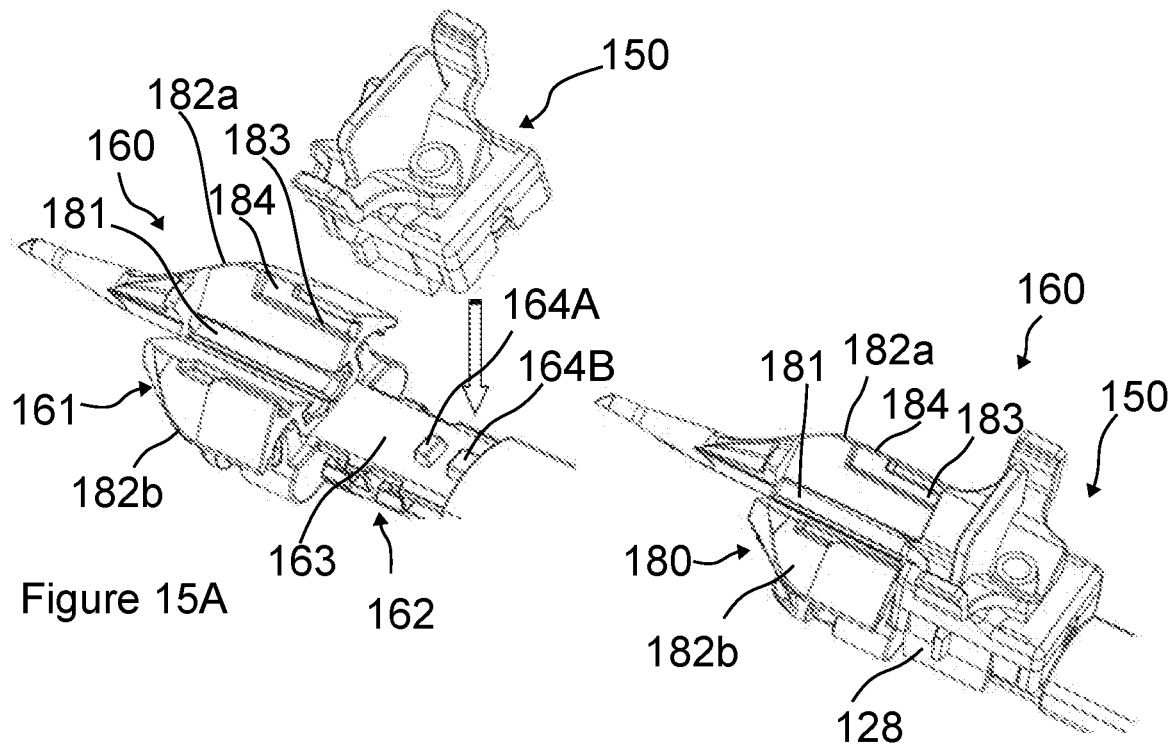
Figure 15A
Figure 15B
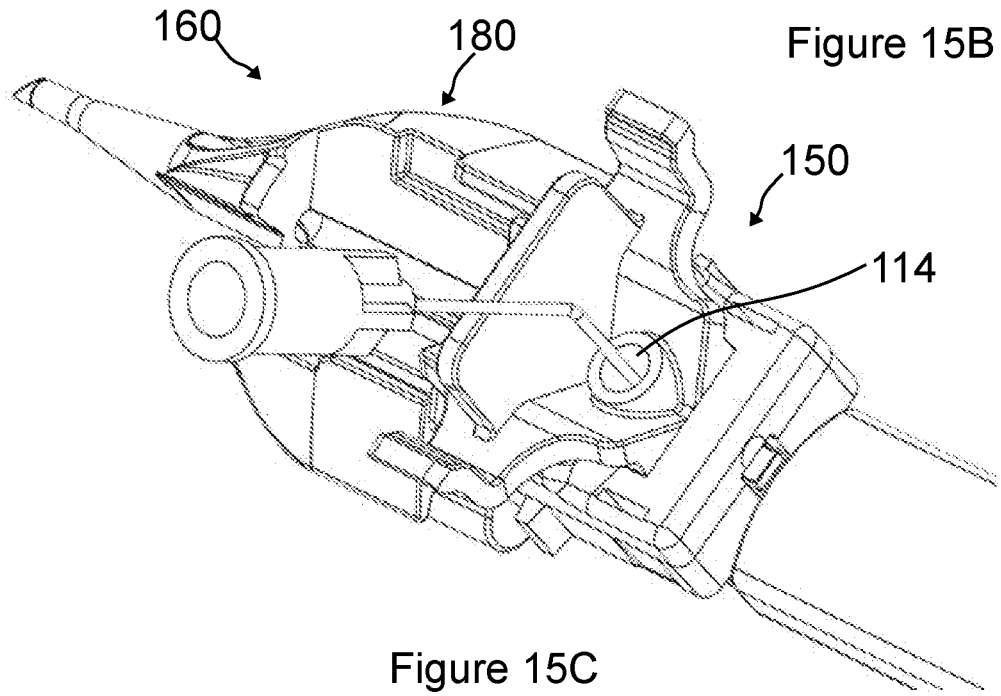
Figure 15C

LENS CASE AND LENS DELIVERY SYSTEM

CROSS-REFERENCE TO RELATED APPLICATIONS

This application is a U.S. National Stage of PCT/HU2018/050055, filed Dec. 28, 2018, which claims priority to PCT/HU2017/000054, filed Dec. 28, 2017, each of which is incorporated herein by reference.

TECHNICAL FIELD

The present invention relates to a lens case for storing an intraocular lens (IOL) and loading the IOL to an injector before injecting the IOL into a patient eye. The invention also relates to a lens delivery system comprising such a lens case.

BACKGROUND

IOLs may be implanted in the eye of a patient to replace the natural crystalline lens or to otherwise modify the vision of an eye containing either the natural lens or another IOL. IOLs commonly include an optic and one or more flexible fixation members, called haptics extending from the optic to secure and center the optic within the eye. When the IOL replaces the natural lens, the natural lens must first be removed. The IOL is then generally implanted using an insertion apparatus or device that rolls, folds, or otherwise configures the lens for delivery through a small incision in the eye—usually called IOL injector—in a way that reduces trauma and expedites post-surgery healing.

The most advanced IOL injector systems for delivering IOLs into the eye are the so-called preloaded IOL/injector systems in which the IOL is preloaded (packed, sterilized and delivered) in the injector to the user. Using these preloaded systems the user does not have to touch the lens before surgery.

Patent specifications U.S. Pat. No. 7,156,854 and WO2007080869 both describe such a preloaded IOL/injector system.

All these preloaded IOL/injector systems have in common that they store the IOL in an unfolded (relaxed) state and by activating the injection/folding mechanism during usage the lens is folded and/or compressed and pushed through a small injection cartridge nozzle into the eye. Preloaded IOL injector systems usually contain IOLs with haptics (fixation members) adapted to the needs of these injection systems. Usually the IOL optic diameter defines the width of the storage space and starting width of the injection channel within the IOL injector. The dimensions and positions of these haptics in relaxed (unfolded) state are fitting into the width of the designed injection channel, usually around 6 mm. This means these IOLs have usually one or two haptics at the front and one or two haptics at the back of the lens, longitudinally to the folding and injection axis.

Patent specifications WO2007027499 and WO2007078602 describe injector systems for hydrophilic IOLs, enabling the user to load the IOL into the injector system without touching the IOL. Both systems can load only IOLs with haptic designs not wider than the IOL optic diameter.

However, the eye structure is circular. Therefore it is clear that a set of haptics of an IOL positioned at the 2 ends of the IOL, creating an IOL whose contact points are not distributed equally around a circle, is not an ideal solution for the anatomy of the eye. The ideal haptics should be evenly distributed around the circle, for example in case of 4 haptics at a distance of 90 degrees to each other. However, such haptic endings widely spread over the width defined by the optic diameter of the IOL. Therefore circularly designed haptics pose a problem in case of preloaded IOLs because an adequate pre-bending and pre-positioning of the haptics has to be accomplished before the optic body of the IOL can be folded or compressed.

Consequently it would be advantageous to provide a lens case and a method which facilitate the adequate pre-bending and pre-positioning of the haptics of the IOL before the compressive impact or folding mechanism of the injector system sets in.

SUMMARY

In accordance with the above objectives the present invention relates to a lens case according to claims 1 and 17 and a lens delivery system according to claim 12.

We realized that safe pre-bending and pre-positioning of the haptics of a foldable intraocular lens (IOL) with a haptics design wider than the IOL optic diameter can be carried out in the lens case itself before the loading of the IOL with unfolded optic into the injector cartridge by applying a sliding element on the lens case that can hold, move and release the IOL within the lens case parallel to the injection axis of the injector system. This sliding element and the method of holding, moving and releasing the IOL can be realized in different ways, in the following we will demonstrate a sliding cap and a bolt which can move the IOL from a first position with relaxed, undistorted haptics into a second position with pre-bent, i.e. pre-distorted haptics within the inner space of the lens case. This movement of the IOL within the lens case is a movement in the counter direction of the direction that the lens will go during injection. This means the haptics are pre-bent (i.e. pre-distorted) on the inner walls of the lens case by retraction of the IOL against the direction which the IOL and its haptics have to take on their way of the injection path.

We also realized that the safe pre-bending and pre-positioning of the haptics of a foldable intraocular lens (IOL) can be carried out automatically in a lens case stored in a container/vial simply during removal of said lens case from the container/vial.

The object of the invention is therefore a lens case for IOLs in which the lens case comprises a lens case body, a sliding element that can hold, move and release the IOL. At least a part of the inner space of the lens case is narrower than the width of the IOL with haptics but larger than the optic diameter of the IOL in a relaxed state. The sliding element can slide on the lens case body.

In an advantageous embodiment the lens case can be placed on a rail in a container/vial, so that by removing the lens case from the container/vial the movement of the IOL from the first to the second position in the lens case is accomplished automatically. In this embodiment the lens case body is provided with a lower portion accommodating a rail of a container/vial, grooves at its sides and, an upper portion accommodating the IOL in an inner space. The sliding cap is also provided with rails fitting into the grooves of the lens case body. The bolt has a lower portion fitting into an opening of the sliding cap. The inner space comprises a first part and a second part. The width of the first part is equal to the width of the IOL with the relaxed, i.e. undistorted haptics and the width of the second part is smaller than the width of the first part.

In other embodiments the lens case can be fixed in an etui or other type of container, dry or wet, for example by a rail.

This construction provides a safe pre-positioning of the IOL and pre-bending of its haptics before loading it into the injector cartridge.

BRIEF DESCRIPTION OF THE DRAWINGS

For a more complete understanding of the invention, reference is made to the following detailed description of an embodiment taken in conjunction with the accompanying drawings wherein:

FIG. 7A is a perspective view, partly in section, showing lens case 50 with IOL 1 removed from rail 6 of container 7, and FIG. 7B is an enlarged perspective view of lens case 50 with optical part 1a of IOL 1 facing direction of injection and showing pre-bent haptics 2 ready for safe loading.

FIG. 13A is a cutaway perspective bottom view of the second embodiment of the lens case in its first position with an uncompressed IOL arranged therein.

FIG. 13.1A is a sectional view of the second embodiment of the lens case taken along cutting plane A-A indicated in FIG. 13A.

FIG. 13B is a cutaway perspective bottom view of the second embodiment of the lens case in its first position with an uncompressed IOL arranged therein.

FIG. 13.1B is a sectional view of the second embodiment of the lens case taken along cutting plane B-B indicated in FIG. 13B.

FIG. 14A is a cutaway view of the container with the second embodiment of the lens case arranged therein in its first position.

FIG. 14.1A is an enlarged view of portion A of FIG. 14A.

FIG. 14B is a cutaway view of the container with the second embodiment of the lens case arranged therein in its second position.

FIGS. 15A and 15B illustrate the mounting of the second embodiment of the lens case on an injector.

FIG. 15C shows the injection of visco-elastic material into the second embodiment of the lens case through an opening of a sliding element.

DETAILED DESCRIPTION

In the following, for purpose of explanation and not limitation, specific details of a lens case for IOLs are set forth, in order to provide a thorough understanding of the present invention. It will be apparent to one skilled in the art that the present invention may be practiced in other embodiments that depart from these specific details.

In our description we continue to present an embodiment with the lens case fixed in a container on a rail.

Figure 1:
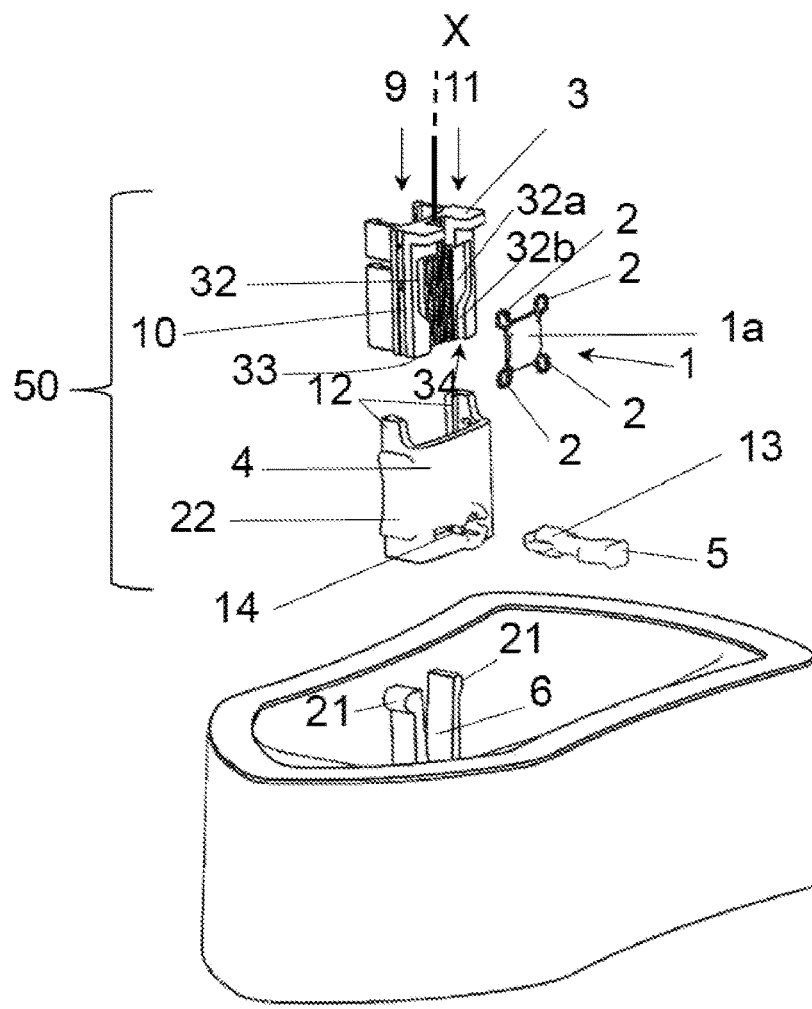
FIG. 1 shows a first embodiment of a lens case according to the invention in disassembled state with a container.
Figure 1A:
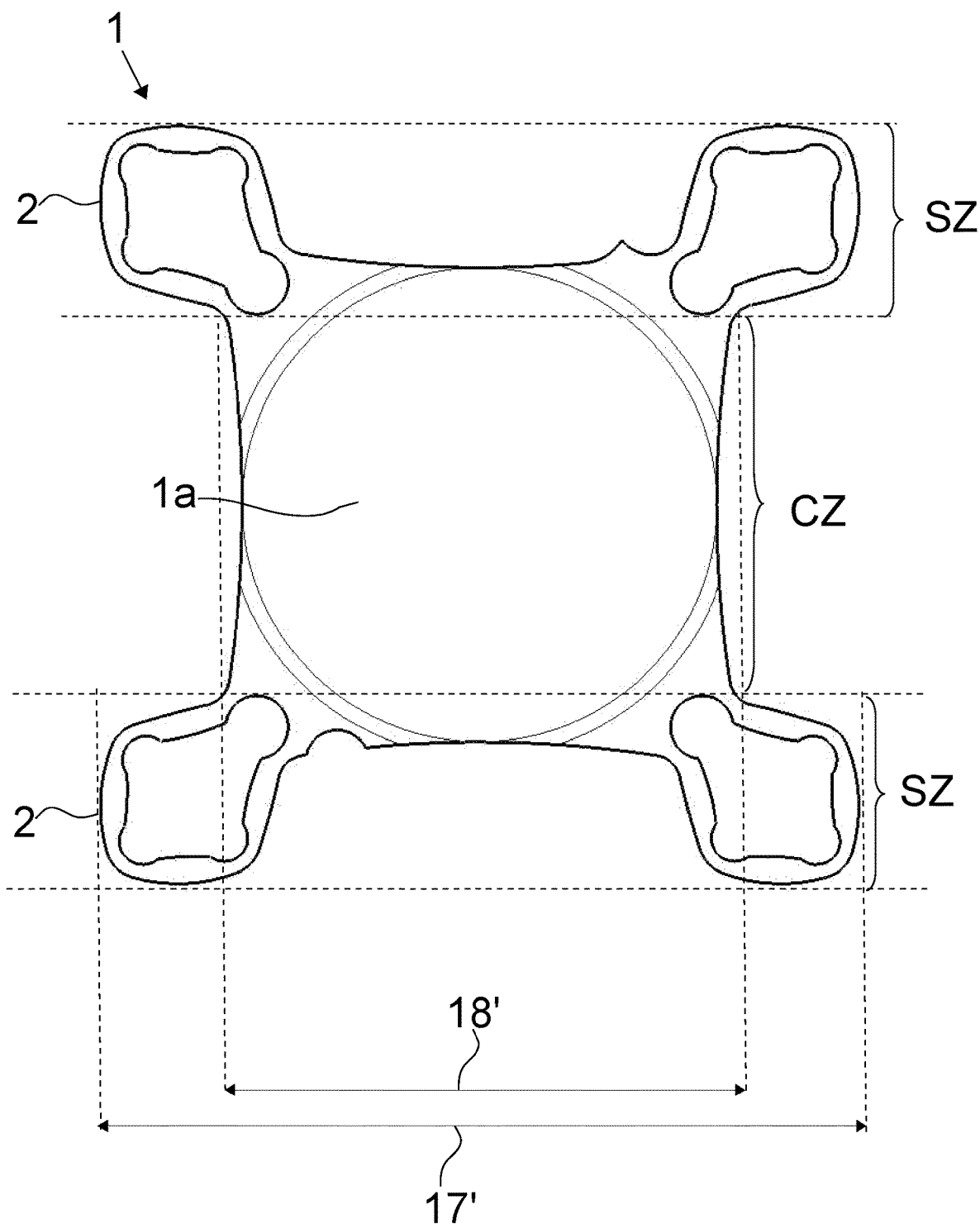
FIG. 1A-1C show exemplary intraocular lenses which can be placed into the lens case.
Figure 1B:
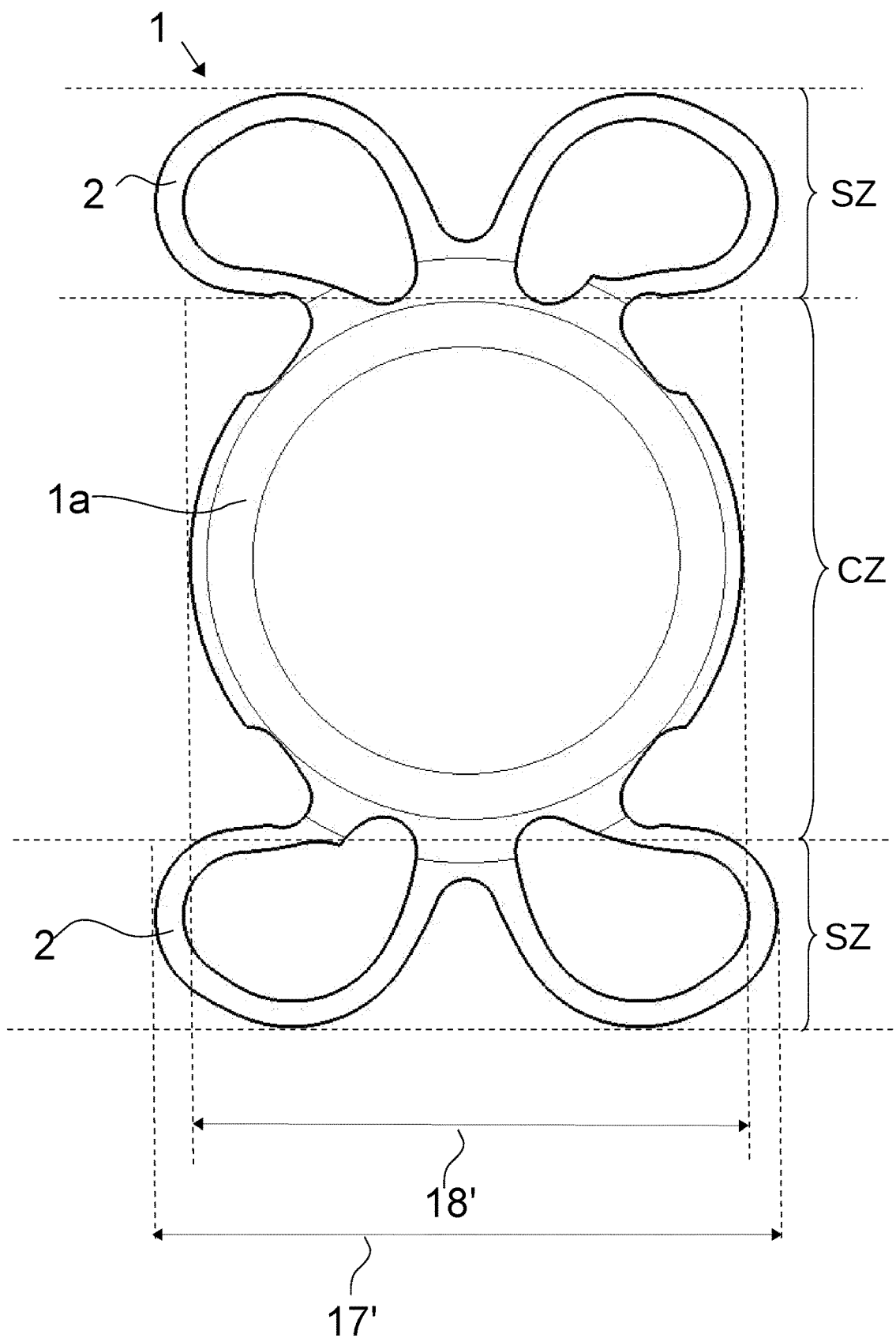
Figure 1C:
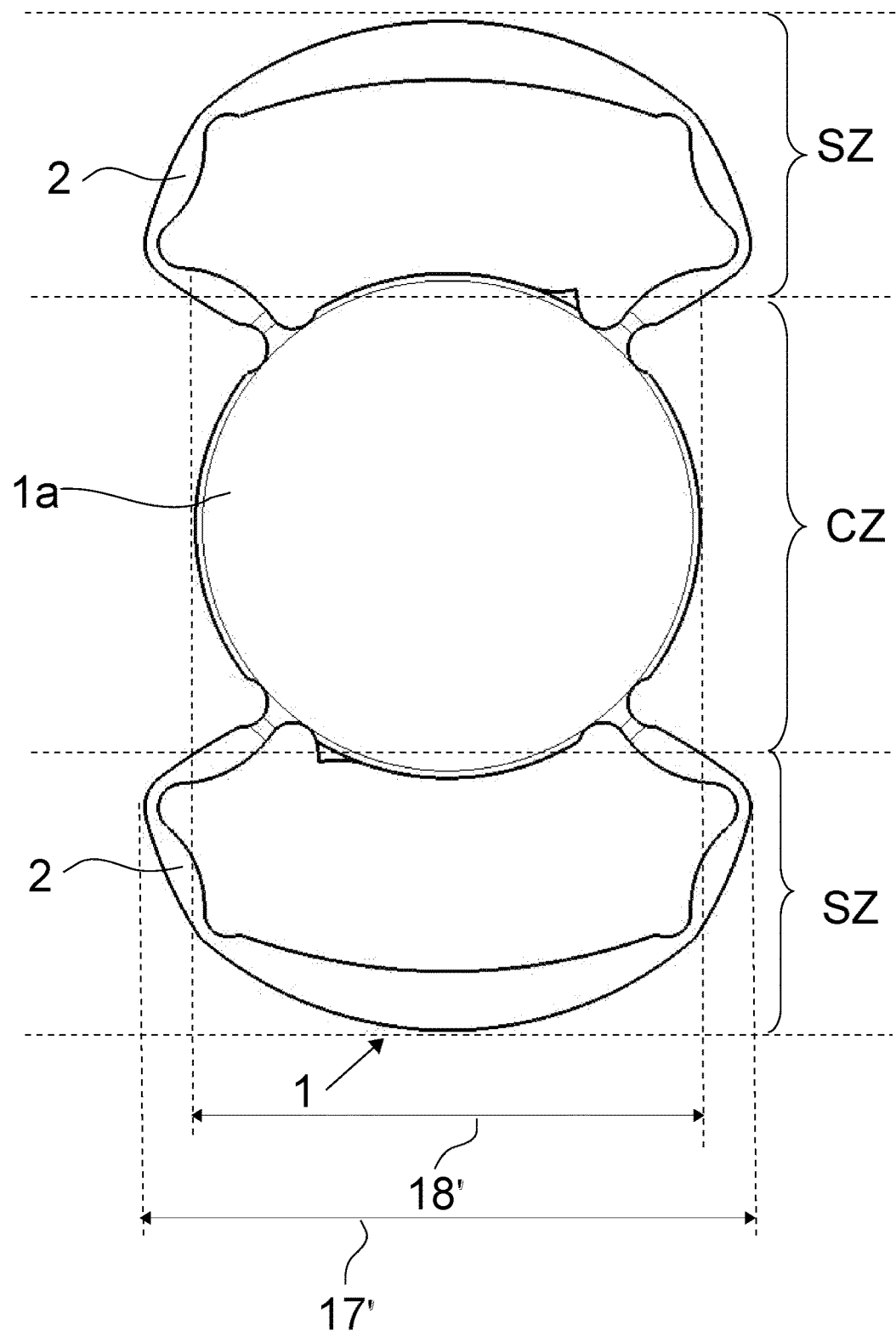

FIG. 1 shows a lens case 50 in disassembled state for storing an intraocular lens (IOL) 1 comprising an optical part 1a and four haptics 2 distributed around the optical part 1a. The IOL 1 is illustrated separately in FIG. 1A. The lens case 50 according to the present invention is designed to pre-fold (pre-distort) the haptics 2 of IOLs 1 consisting of a central zone CZ substantially free of any haptics 2 and two side zones SZ on each side of the central zone CZ, each side zone SZ comprising at least one haptic 2, in the present case two haptics 2, as illustrated in FIG. 1A. A width 17' of each side zone SZ with relaxed haptics 2 is greater than a width 18' of the central zone CZ, which corresponds practically to the width of the optical part 1a. Further IOLs 1 with such configuration are illustrated in FIGS. 1B and 1C. Such IOLs have a shape that does not allow the uncompressed IOL 1 to pass through an opening with a width corresponding to the width of the optical part 1a. This makes the operation of loading such an IOL 1 into an injector and subsequently injecting it in an eye very difficult as the haptics 2 extending beyond the width of the optical part 1a can get jammed easily.

The lens case 50 comprises a lens case body 3 having a longitudinal axis X, a sliding element in the form of a sliding cap 4, which is provided with a bolt 5. The lens case body 3 is provided with a lower portion 9 accommodating a rail 6 of a container 7, and longitudinal grooves 10 at its sides being parallel with the longitudinal axis X, and an upper portion 11 accommodating the IOL 1 within a longitudinal recess 32. The sliding cap 4 is provided with rails 12 received by the grooves 10 of the lens case body 3. The bolt 5 is provided with a lower portion 13 fitting in an opening 14 of the sliding cap 4. The sliding cap 4 is provided with grips 22 at both sides for a better clutch with fingers. The rail 6 of the container 7 has two resilient bumpers 21 at the end thereof for fixing the lens case 50 in the container 7.

Figures 3A, 3B, 3C:
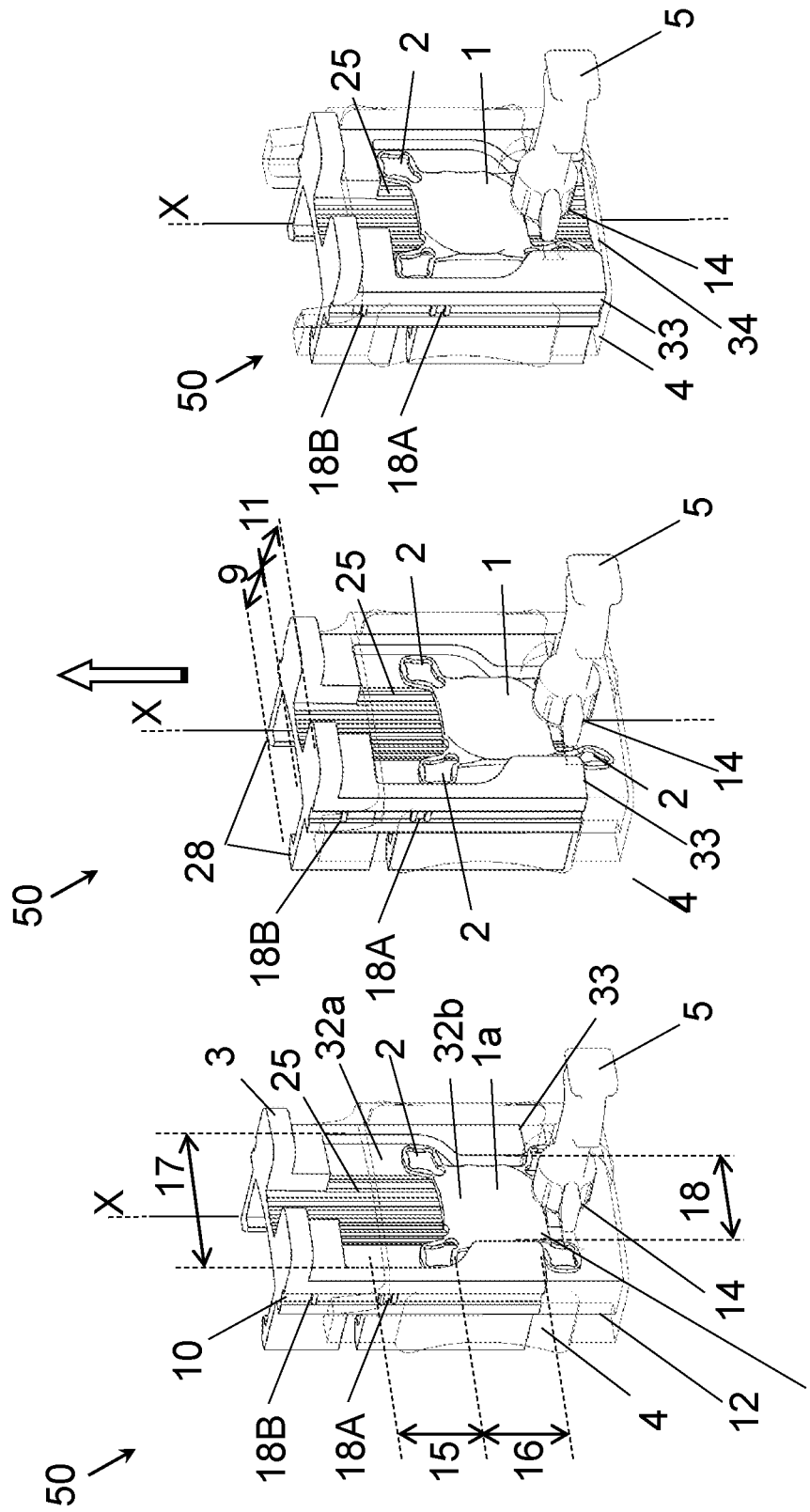
FIGS. 3A, 3B, 3C show the three phases of the sliding cap with the bolt on the lens case body moving from a first position to a second position.

The lens case body 3 comprises a first end 33 provided with a loading port 34 perpendicular to the longitudinal axis X. The longitudinal recess 32 has a first part 32a and a second part 32b provided along the longitudinal axis X. The second part 32b of the recess 32 terminates in the loading port 34, whereby the second part 32b of the recess 32 is accessible from the first end 33 of the lens case body 3 through the loading port 34. As can be seen in FIG. 3A the first part 32a has a first width 17 being greater than a width of the IOL 1 with relaxed haptics 2, and the second part 32b has a second width 18 being narrower than the width of the IOL 1 with relaxed haptics 2 but larger than a width of the optical part 1*a* of the IOL 1 in a relaxed state. Since the optical part 1*a* of most IOLs 1 are between 4 to 8 mm, generally between 6 to 7 mm, accordingly the second width 18 is preferably greater than 4 mm and smaller than 8 mm, more preferably greater than 6 mm and smaller than 7 mm.

Figure 2:
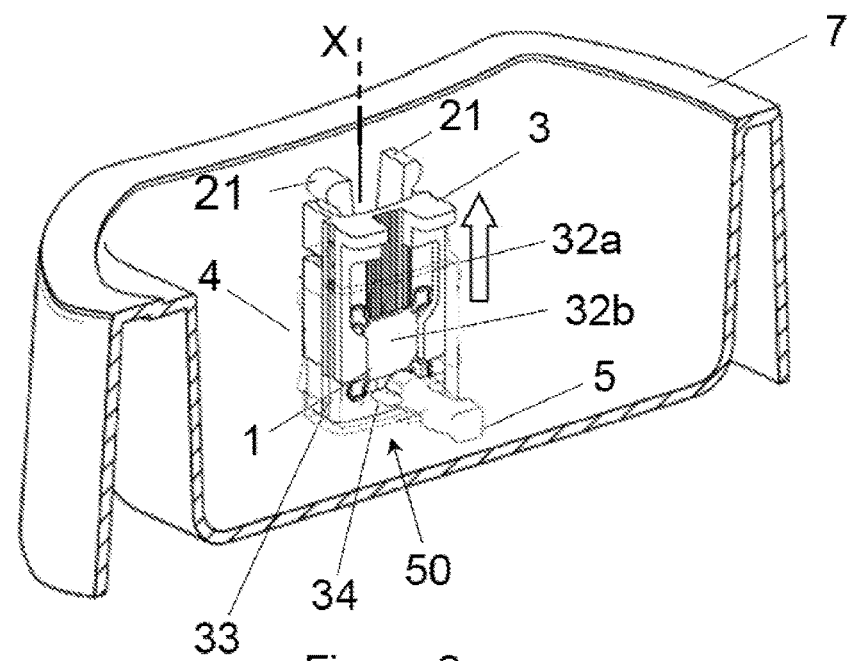
FIG. 2 shows the lens case in assembled state with a container.

FIG. 2 shows the lens case 50 in assembled state with the container 7. The container 7 is shown in a section view to reveal the lens case 50 with the lens case body 3, the sliding cap 4 and the bolt 5. The sliding cap 4 is attached to the lens case body 3 and the bolt 5 is inserted in the sliding cap 4 which is illustrated transparently to make the IOL 1 visible inside the lens case 50. The bumpers 21 prevent the lens case 50 to move in the container 7 unintentionally indicated by the arrow.

FIGS. 3A, 3B, 3C show three positions of the sliding cap 4 on the lens case body 3 as the sliding cap 4 is moved from a first position to a second position. The first position is shown in FIG. 3A while the second position is shown in FIG. 3C. FIG. 3B depicts an intermediate position between the first position and the second position. The recess 32 in the upper portion 11 of the lens case body 3 forms together with the sliding cap 4 an inner space 25 having a first part 15 (corresponding to the first part 32*a* of the recess 32) and an second part 16 (corresponding to the second part 32*b* of the recess 32). The width 17 of the first part 15 of the inner space 25 (corresponding to the width 17 of the first part 32*a* of the recess 32) is equal to or wider than the width of the IOL 1 with the undistorted haptics 2 and the width 18 of the second part 16 of the inner space 25 (corresponding to the width 18 of the second part 32*b* of the recess 32) is smaller than the width 17 of the first part 15. The lower portion 9 of the lens case body 3 comprises flanges 28. There are rails 12 on the sliding cap 4 that can slide on grooves 10 of the lens case body 3. It is not shown in FIGS. 3A-3C but the guide 10 of the lens case body 3 and the guide 12 of the sliding cap 4 are provided at both sides of the lens case body 3 and the sliding cap 4, respectively. The guide 10 of the lens case body 3 is a groove and the guide 12 of the sliding cap 4 is a rim but in another embodiment the guide 10 of the lens case body 3 can be a rim and the guide 12 of the sliding cap 4 can be a groove.

In order to separate the first position of the sliding cap 4 on the lens case body 3 from the second position thereof, a first stopper 18A on the guide 10 of the lens case body 3 provides an anchor for the first position to the sliding cap 4 in which the bolt 5 in the opening 14 of the sliding cap 4 positioned outside of the inner space 25 (in FIG. 3A), and a second stopper 18B on the guide 10 of the lens case body 3 provides another anchor for the second position to the sliding cap 4 in which the bolt 5 in the opening 14 of the sliding cap 4 is positioned within the inner space 25 (in FIG. 3C). The arrow in FIG. 3B shows the moving direction of the sliding cap 4. The sliding cap 4 is illustrated transparently to show the IOL 1 inside the lens case 50.

Figure 4A:
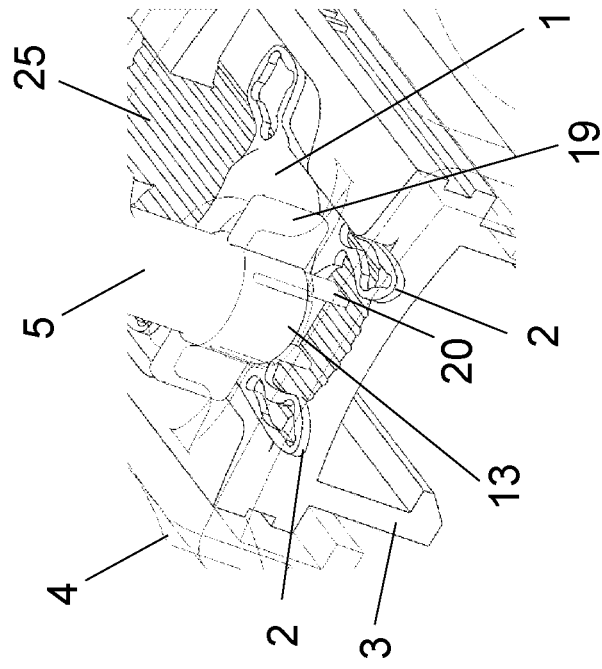
FIGS. 4A, 4B show the pre-bending, i.e. pre-distortion phases of the haptics of the IOL while the sliding cap with the bolt is moving from the first position to the second position thereof, moving the IOL against the direction of injection.
Figure 4B:
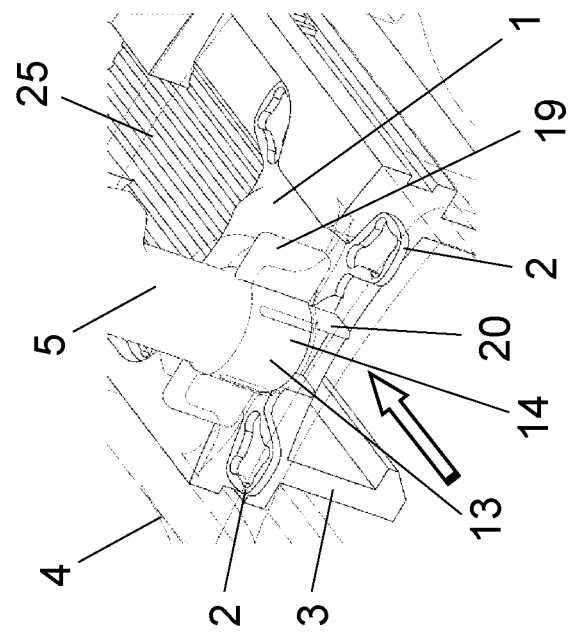

FIGS. 4A, 4B show the pre-distortion phases of the haptics 2 of the IOL 1 while the sliding cap 4 is moving from the first position to the second position. In FIG. 4A, the haptics 2 are in undistorted state, in FIG. 4B the haptics are in distorted state. Distortion is made possible by the different widths of the first and the second parts of the inner space 25.

A lower portion 13 of the bolt 5 is provided with a protrusion 19, the width of which is wider than the width of the opening 14 in the sliding cap 4. The bolt 5 is provided with a leg 20, the bottom of which comes close to the bottom of the inner space 25 when the bolt 5 is inserted in the opening 14 of the sliding cap 4. In this way, the bolt 5 can move the IOL 1 in the inner space 25 when the sliding cap 4 moves on the lens case body 3.

Figure 5:
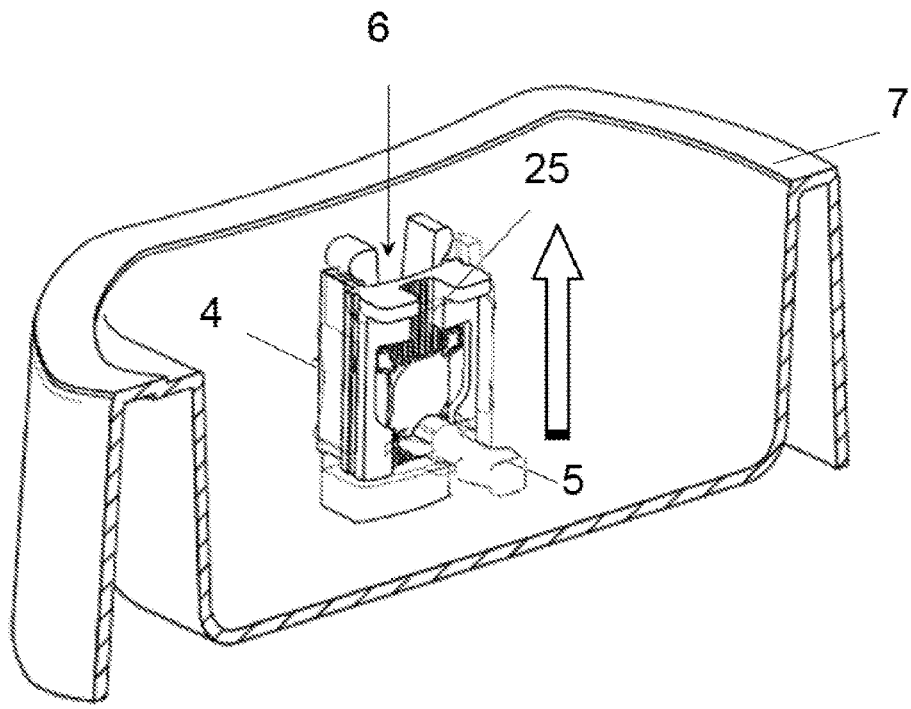
FIG. 5 shows the lens case before removing it from a container.

FIG. 5 shows the lens case 50 before removing it from the container 7. The container 7 is shown in a sectional view. In this state, the lens case 50 is in the second position, when the bolt 5 lies within the inner space 25 as discussed in connection with FIG. 3C. The arrow shows the direction to remove the lens case 50 from the container 7.

Figures 6A, 6B:
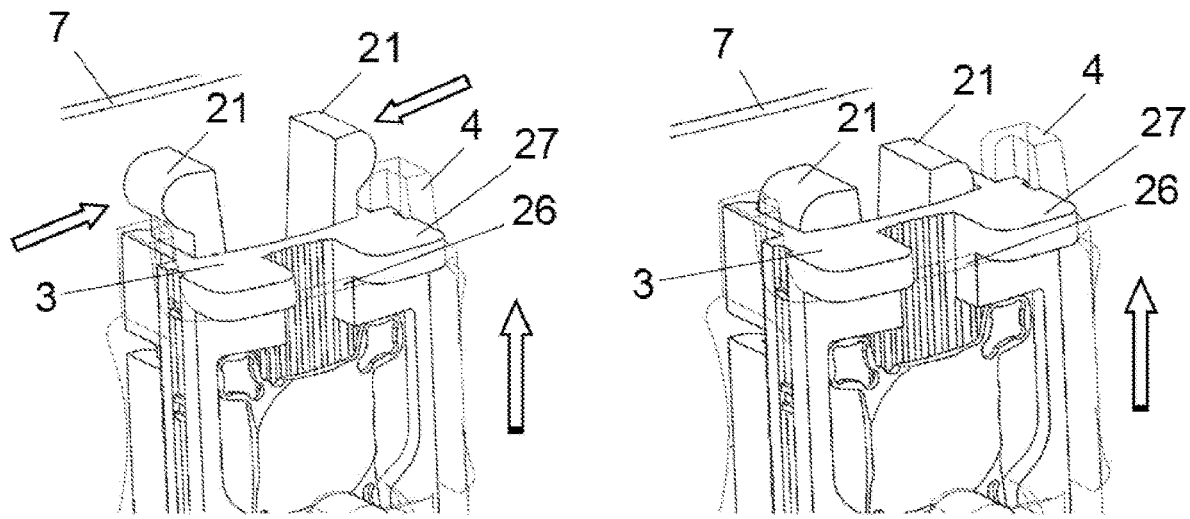
FIGS. 6A and 6B show the moving of the lens case against the bumpers of the rail of the container.

FIGS. 6A and 6B show the moving of the lens case 50 against the bumpers 21 of the rail of the container 7. The sliding cap 4 is in the second position and an edge 26 of the sliding cap 4 abuts a collar 27 of the lens case body 3. By moving the lens case 50 further upwards as shown by the vertical arrow in FIGS. 6A and 6B, the bumpers 21 are getting closer to each other as illustrated by the horizontal arrows. At the end, the bumpers 21 are sufficiently close to each other to release the lens case 50 from the container 7.

FIG. 7 shows the lens case 50 with the retracted IOL 1 with pre-bent (distorted) haptics 2 after removal of the lens case 50 from the rail 6 of the container 7. In this embodiment, two haptics 2 of the IOL 1 facing the injection direction are pre-distorted ready for a safe loading.

Figure 8B:
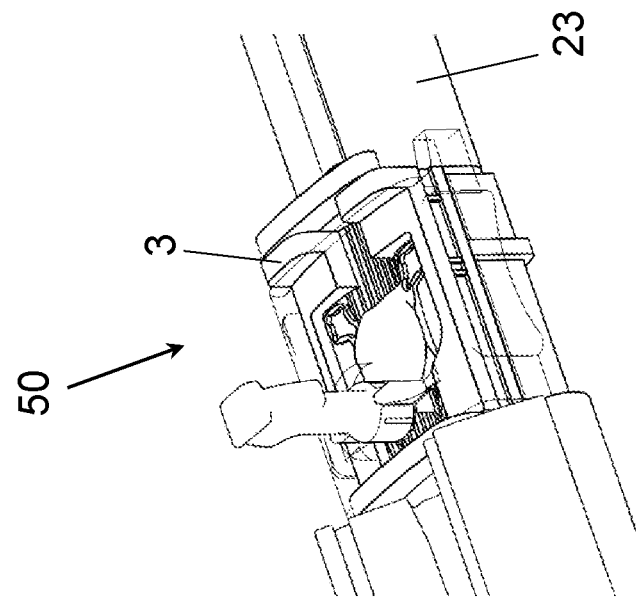
FIGS. 8A, 8B show the mounting of the lens case on an injector.
Figure 8A:
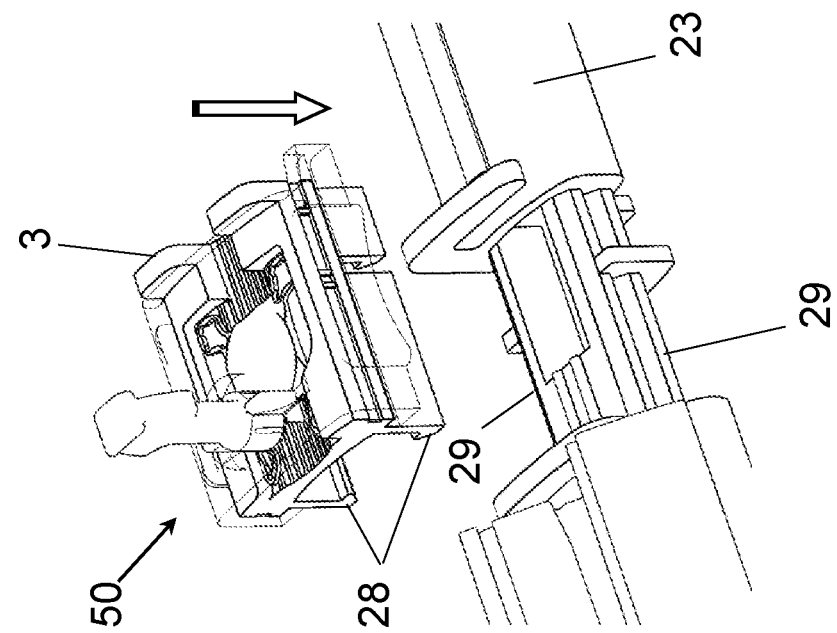

FIGS. 8A, 8B show the mounting of the lens case 50 on an injector 23. The lens case body 3 is provided with flanges 28 at its bottom portion fitting to recesses 29 on the injector 23. Arrow shows the direction of placement. In FIG. 8B, the lens case 50 can be seen mounted on the injector 23.

Figure 9:
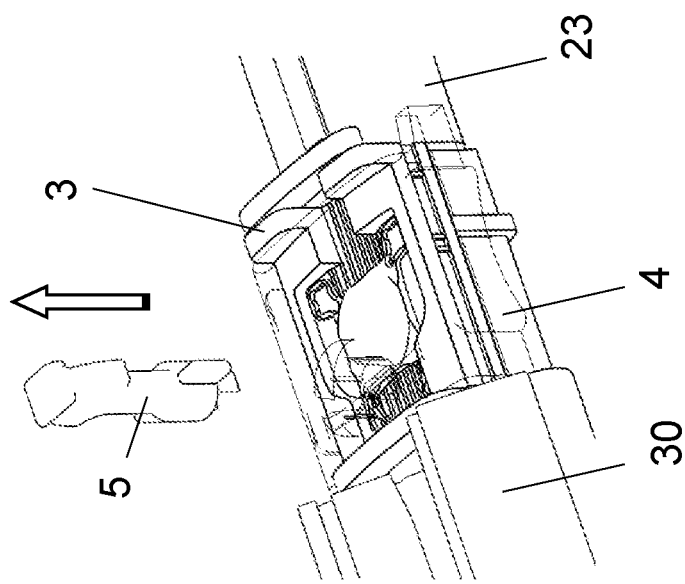
FIG. 9 shows the removal of the bolt from the lens case.

FIG. 9 shows the removal of the bolt 5 from the lens case 50. After removal, the path of the IOL 1 is free in the direction leading to a cartridge 30 of the injector 23.

Figure 10:
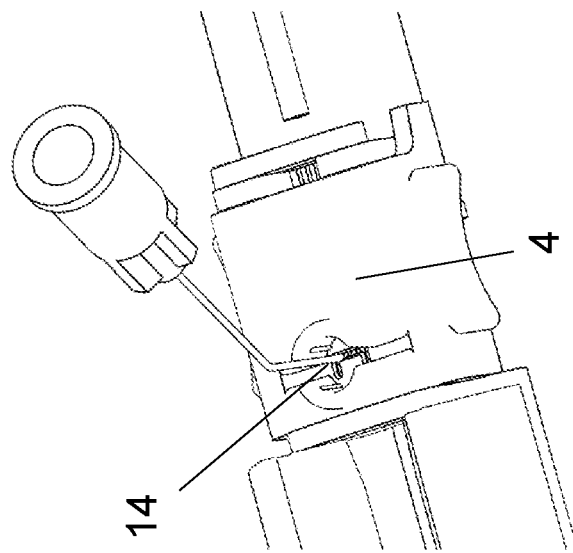
FIG. 10 shows the injection of visco-elastic material into the lens case through the opening of the sliding cap.

FIG. 10 shows the injection of visco-elastic material into the lens case 50 through the opening 14 of the sliding cap 4. Visco-elastic material decreases the friction of the IOL during loading and injecting.

The IOL 1, illustrated in the previous figures, comprises four haptics 2 but the lens case 50 can be adapted to accommodate IOL 1 with two or more haptics 2 as well.

The invention also relates to a method of operating a lens case 50 comprising a lens case body 3 with inner space 25, a sliding cap 4 and a bolt 5. The method comprises when using the above described embodiment the following steps are carried out:

a.) sliding the sliding cap 4 via the bolt 5 along the lens case body 3 within the container 7 until the sliding cap 4 moves from the first position to the second position on the lens case body 3 thereby displacing the IOL 1 from the first part 15 of the inner space 25 to the second part 16 of the inner space 25 (FIGS. 3A-3C and FIGS. 4A, 4B); in this step the IOL is retracted along the longitudinal axis X, i.e. moved in counter-direction to the injection direction of the IOL, while the haptics 2 of the IOL facing the injection direction are pre-bent (distorted).

b.) removing the lens case 50 from the container 7 by pulling it from the rail 6 of the container 7 against resilient bumpers 21 (FIG. 5, FIGS. 6A, 6B and FIG. 7); in this step the resilient bumpers 21 come close to each other allowing the lens case 50 to be removed from the container 7.

c.) mounting the lens case 50 on an injector 23 (FIGS. 8A, 8B); in this step, the flanges 28 at the bottom of the lens case body 3 are attached to recesses 29 of the injector 23.

d.) removing the bolt 5 from the sliding cap 4; in this step, the path of the IOL 1 is freed to a cartridge 30 of the injector 23.

e.) injecting visco-elastic material into the lens case 50 through the opening 14 of the sliding cap 4 (FIG. 10) to decrease the friction of the IOL during loading and injecting.

In another embodiment when the lens case 50 is not fixed in any container or vial the lens case 50 can be operated by manually moving the sliding cap 4 of the lens case 50 against the lens case body 3. In such an embodiment the steps of the method are as follows.

a.) sliding the sliding cap 4 via the bolt 5 along the lens case body 3 until the sliding cap 4 moves from the first position to the second position on the lens case body 3 thereby retracting the IOL 1 along the longitudinal axis X, i.e. moving it in counter-direction to the injection direction of the IOL, thereby bending the haptics 2 of the IOL facing the injection direction from a relaxed state to a distorted state.

b.) mounting the lens case 50 on an injector 23;

c.) removing the bolt 5 from the sliding cap 4;

d.) injecting visco-elastic material into the lens case 50 through the opening 14 in the lens case 50 cap 4.

A second preferred embodiment of the invention is shown in FIGS. 11 to 17.

Figures 11, 12:
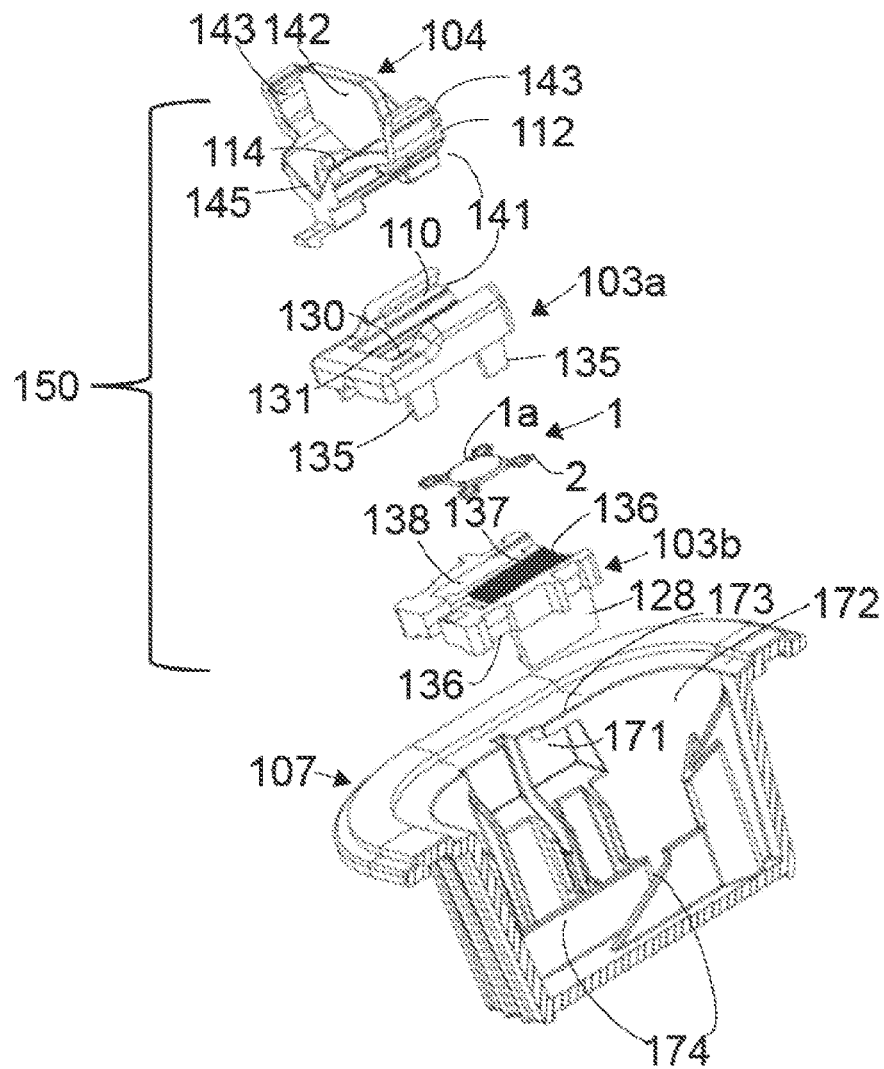
FIG. 11 is an exploded view of a second preferred embodiment of a lens case and container according to the invention.
FIG. 12 is a perspective view of the assembled second embodiment of the lens case.

FIG. 11 is an exploded view of the second embodiment of a lens case 150 according to the invention and a cutaway view of a container 107 for storing the lens case 150. An exemplary IOL 1 is also depicted for which the same reference numerals are used as in the case of the first embodiment. The lens case 150 is shown in an assembled state in FIG. 12.

The lens case 150 comprises a sliding element 104 and a lens case body 103. The lens case body 103 has a first end 133 with a loading port 134 provided therein through which the IOL 1 may be loaded into an injector. The lens case body 103 has an upper part 103a and a lower part 103b. A snap fit connection is provided between the upper part 103a and the lower part 103b of the lens case body 103 which, in the case of the present embodiment, is in the form of four profiled projections 135 and four correspondingly shaped recesses 136 provided on the two sides of the upper part 103a and the lower part 103b, respectively. A recess 132 is formed between the upper part 103a and the lower part 103b of the lens case body 103 and communicates with the loading port 134 at the first end 133 of the lens case body 103 (see FIGS. 13A and 13B where the lower part 103b of the lens case body 103 is indicated transparently and the bottom portion of the lower part 103b is cut away in order to show the position of the IOL 1). According to the present embodiment a first part 132a of the recess 132 is defined by a top surface of a bottom plate 137 and two side rims 138 of the lower portion 103b of the lens case body 103 (see FIG. 11) and a second part 132b of the recess 132 is defined by the bottom plate 137 of the lower portion 103b and two longitudinal protrusions 139 of the upper portion 103a of the lens case body 103 (see FIGS. 13A and 13B).

The first width 17 of the first part 132a of the recess 132 is greater than the width 17' of the side zone SZ of the IOL 1 in order to receive therein one of the side zones SZ. The second part 132b of the recess 132 communicates with the loading port 134. The second width 18 of the second part 132b of the recess 132 is greater than the width 18' of the central zone CZ of the IOL 1 but smaller than the width 17' of the side zones SZ in order to accommodate the central zone CZ (which is mainly the optical part 1a) in an uncompressed state. A width of the loading port 134 preferably equals the width of the second part 132b of the recess 132.

A sliding connection 141 is provided between the lens case body 103 and the sliding element 104 for sliding the sliding element on the lens case body 3 along a longitudinal axis X of the lens case 150 from a first position (indicated in FIG. 13A) to a second position (indicated in FIG. 13B). The sliding connection 141 is preferably in the form of grooves 110 provided on the lens case body 103 and rails 112 provide on the sliding element 104. In the first position of the sliding element 104 the IOL 1 is held within the recess 132 of the lens case body 103 in a relaxed state such that the central zone CZ lies within the second part 132b of the recess 132, a first one of the side zones SZ is received in the first part 132a and a second one of the side zones SZ extends from the recess 132 through the loading port 134 as shown in FIG. 13A. In the second position of the sliding element 104 depicted in FIG. 13B the IOL 1 is displaced such that the side zone SZ previously extending outside of the loading port 134 is now retracted into the second part 132b of the recess 132, while most part or all of the central zone CZ has moved into the first part 132a of the recess 132 along the longitudinal axis X. The sliding element 104 comprises a first bolt 105a arranged adjacent the loading port 134 for effecting the displacement of the IOL 1 within the recess 132 of the lens case body 103. In the first position of the sliding element 104 the first bolt 105a is outside of the recess 132, preferably abutting the IOL 1 and in the second position of the sliding element 104 the first bolt 105a extends into the second part 132b of the recess 132.

The sliding element 104 is preferably provided with an upper tab 142 by which a user can grab and push the sliding element 104 in the direction of the arrow illustrated in FIG. 14A when the lens case 150 is arranged in the container 107. The sliding element is further provided with two sidewardly projecting resilient winglets 143 adapted to cooperate with two recesses 171 formed in opposing sides of a wall 172 of the container 107 of which only one is illustrated in the cutaway view of FIG. 14A. In the first position of the sliding element 104 the winglets 143 snap into the recesses 171 and an upper rim 173 of the recesses block upward movement of the winglets 143 as indicated in FIG. 14.1A and thereby retain the lens case 150 within the container 107. As the tab 142 of the sliding element 104 is pushed in the direction of the arrow C in FIG. 14A, the sliding element 104 slides on the lens case body 103 via the sliding connection until it reaches its second position illustrated in FIG. 14B where the winglets 143 are no longer underneath the rim 173 of the recess 171, whereby the lens case can be lifted in the direction of the arrow C as illustrated in FIG. 14B.

According to the present embodiment first and second stoppers 118A and 118B are provided on the lower part 103b of the lens case body 103 in the form of openings for locking the first and second position of the sliding element 104. The sliding element 104 is provided with a resilient cantilever hook 144 which snaps into the opening 118A in the first position of the sliding element 104 and snaps into the opening 118B in the second position of the sliding element 14 as best seen in FIGS. 13.1A and 13.1B, respectively. The cantilever hook 144 is designed to snap out of the opening 118A if the sliding element 104 is displaced from the first position in the direction of the second position as indicated with arrow C in FIGS. 13A and 13.1A but prevents displacement in the opposite direction. Consequently, once the sliding element 104 reaches its second position it is no longer possible to return the sliding element 104 in its first position. The sliding element 104 cannot be advanced any further than the second position as a front face 145 of the sliding element 104 abuts a front rim 131 of the upper portion 103a of the lens case body 103 as best seen in FIG. 14B.

The lower portion 103b of the lens case body 103 is preferably provided with two profiled projections 128 for attaching the lens case 50 to an injector 123. The container 107 is provided with spacers 174 for spacing the lens case body 103 and thereby the profiled projections 128 from the bottom of the container 107.

According to the second embodiment the sliding element 104 is further provided with a second bolt 105b which extends into the first part 132a of the recess 132 of the lens case body 103 through a longitudinal central opening 130 of the upper portion 103a. The first and the second bolt 105a, 105b are spaced from each other such as to accommodate the IOL 1 there between as best seen in FIGS. 13A and 13B. The cantilever hook 144 is provided on the second bolt 105b. The second bolt 105b serves to displace the IOL 1 in the counter-direction of the arrow C illustrated in FIG. 13A once the cantilever hook 144 is removed from the stopper 118A.

The sliding element 104 is further provided with a funnel 146 having a wider opening 114 at the top face of the sliding element 104 and terminating in a through hole 147 traversing the second bolt 105b for injecting visco-elastic material into the recess 132 of the lens case body 103. FIGS. 15A to 17B illustrate the loading of the IOL 1 from the lens case 150 into a cartridge 180 of an injector 160.

The injector 160 is provided with a receiving part 162 for receiving the lens case 150 as illustrated in FIGS. 15A-15C. The receiving part 162 has an upper surface 163 with a first and a second protrusions 164A and 164B fitting into the first and second openings 118A and 118B, respectively. The first and second protrusions 164A and 164B have a height ensuring that the top faces of the first and second protrusions 164A and 164B are level with the top surface of the bottom plate 137 of the lower portion 103b of the lens case body 103 when the lens case 150 is placed on the top surface 162 of the receiving part 160 of the injector 160 and the first and second protrusions 164A and 164B project into the first and second openings 118A and 118B respectively. This has for effect that the resilient cantilever hook 144 of the sliding element 104 is forced out of the opening 118B by the second protrusion 164B, whereby the sliding element 104 can be moved from its second position in the direction of its first position, which is the counter-direction of the arrow C depicted in FIGS. 13A and 13.1A. Since the top surface of the second protrusion 164A is level with the upper surface of the bottom plate 137 the sliding element can be slid past its first position as the cantilever hook 144 is prevented by the first protrusion 164A from snapping back into the first opening 118A.

The cartridge 180 of the injector 160 has a lens receiving channel 181 and two winglets 182a and 182b. The lens receiving channel 181 has a width corresponding to the width 18 of the second part 132b of the recess 132 of the lens case body 103. The lens receiving channel 181 is level with the recess 132, whereby the IOL 1 may be slid from the recess 132 into the channel 181 upon pushing force exerted by the second bolt 105b. The lens receiving channel 181 need not have a planar receiving surface. A second sliding connection is provided between the cartridge 180 and the sliding element 104, which is formed by the rails 112 of the sliding element 112 and a groove 183 in each winglet 181a, 181b. The distal end of the grooves 183 are formed with a longitudinal exit port 184 a length of which corresponds to a length of the rails 112 of the sliding element 104. In an end position of the sliding element 104 the rails 112 reach the exit port 184, whereby the rails 112 are released and the sliding element 104 can be lifted from the cartridge 180.

When the lens case 150 is received in the receiving part 162 of the injector 170 the sliding element 104 can be slid from the receiving part 162 onto the cartridge 180 of the injector 170.

Figure 16A:
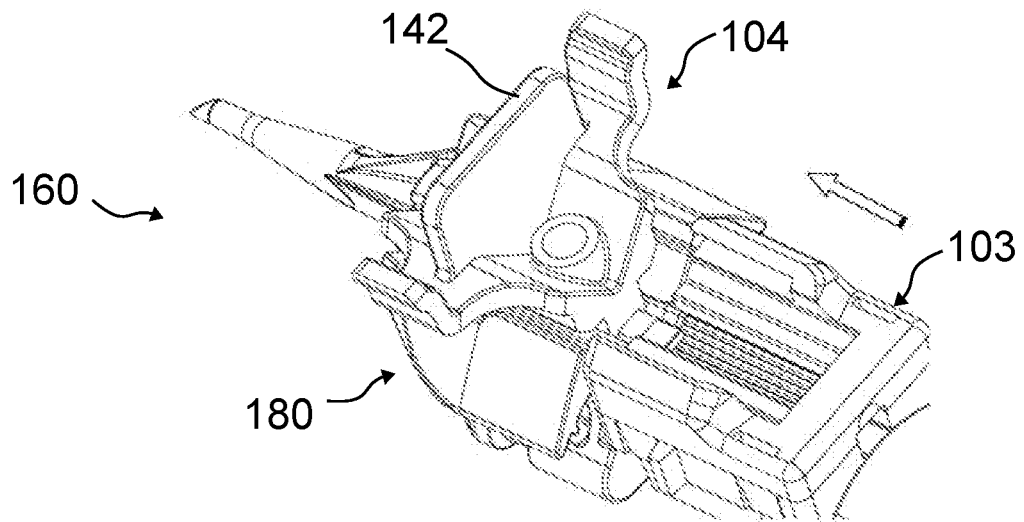
FIG. 16A shows the sliding of the sliding element over a cartridge of the injector.
Figure 16B:
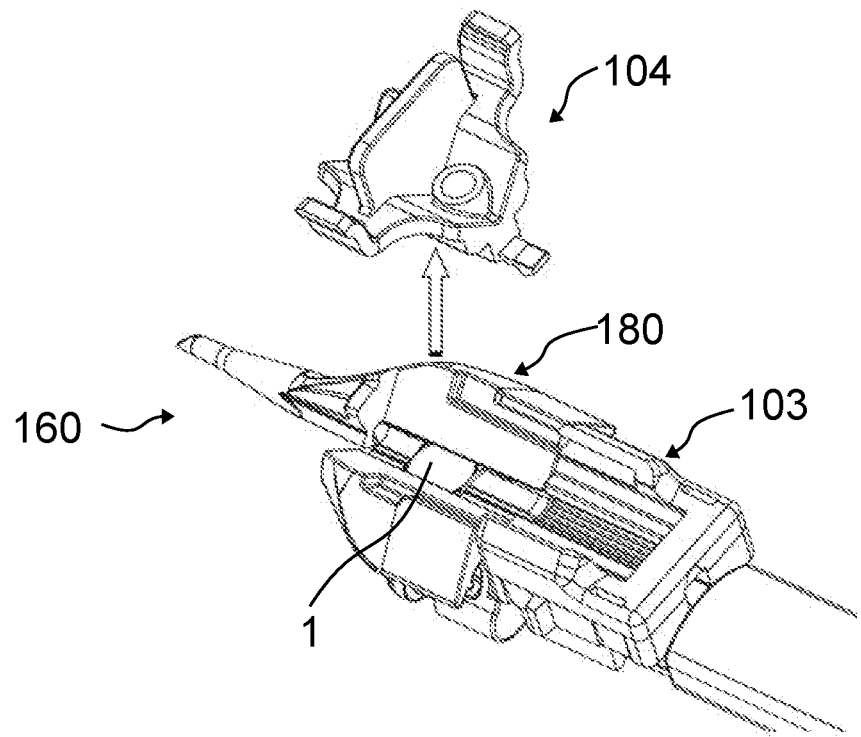
FIG. 16B illustrates the removal of the sliding element from the injector.
Figure 17A:
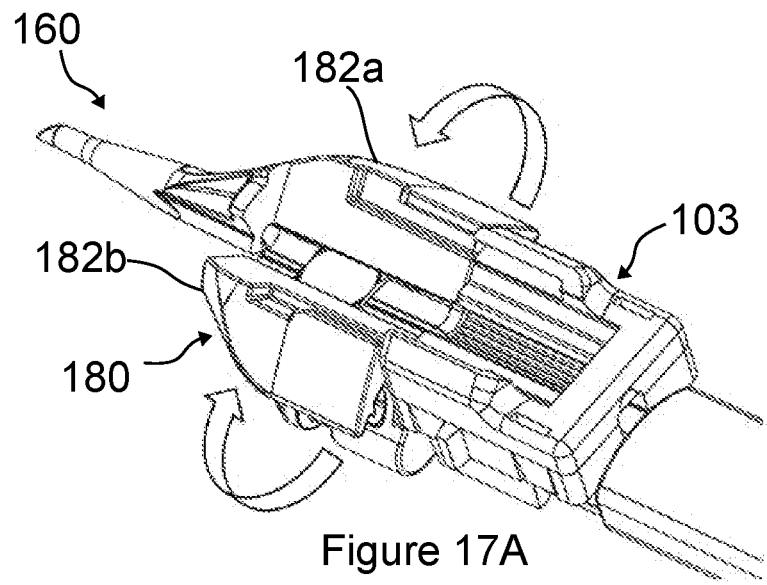
FIGS. 17A-17B illustrate the folding of the IOL by closing the winglets of the injector's cartridge.
Figure 17B:
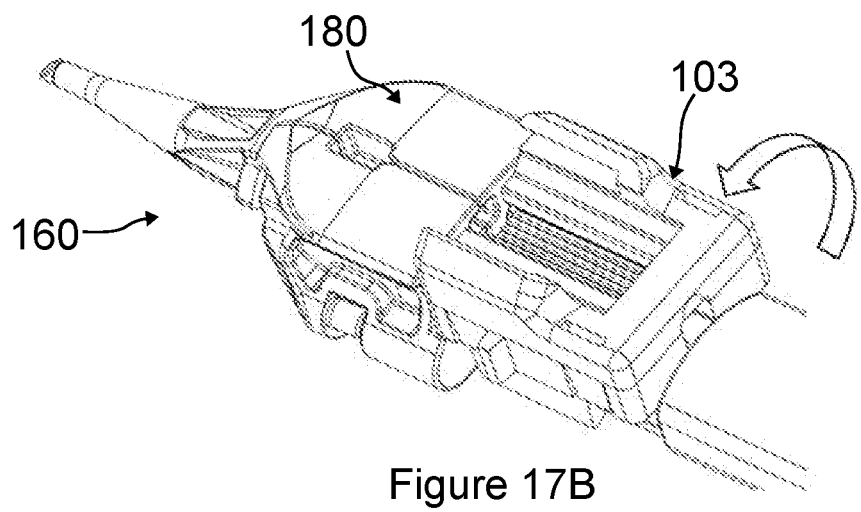

Before starting to slide the sliding element 104 visco-elastic material is injected into the recess 132 of the lens case body 103 through the opening 114 as shown in FIG. 15C. The visco-elastic material helps to reduce friction between the IOL 1 and the bottom plate 137 of the lens case body 103 as the sliding element 104 is slid from the lens case body 103 to the cartridge 180 (see FIG. 16A) and the IOL 1 is carried along by the second bolt 105b of the sliding element 104 into the cartridge 180. The cartridge 180 has an inner width corresponding to the width 18 of the second recess 132b and the haptics 2 of the IOL 1 pre-folded in the second recess 132b can easily enter the cartridge 180 through the loading port 134 of the second recess 132b without being jammed or distorted in any unintended configuration. Once the IOL 1 has been loaded into the cartridge 180 the sliding element is removed therefrom as illustrated in FIG. 16B. The optical part 1a of the IOL 1 is further folded by closing two winglets 182a and 182b of the cartridge 180 as depicted in FIGS. 17A and 17B.

It may be clear from the description above and the accompanied figures that the lens case 50, 150 according to the invention can provide a safe pre-distortion for haptics 2 of an IOL 1 and so minimizes the risk of jamming the IOL during loading and insertion. Additionally, the described embodiment presents some advantageous details too. For instance, the step of moving the sliding cap 4 from a first position to a second position and thereby retracting the IOL, pre-distorting the haptics 2 of the IOL 1, and the step of removing the lens case 50 from the container 7 are practically a single motion. Another advantageous detail is the function of the opening 14 in the sliding cap 4. On one hand the opening 14 accommodates the bolt 5, on the other hand it makes an inlet for injection of visco-elastic material too.

Although two preferred embodiments of the present invention have been illustrated in the accompanying drawings and described in the foregoing detailed description, it is understood that the invention is not limited to the disclosed embodiments but is capable of numerous rearrangements, modifications, and substitutions for the lens case 50 without departing from the invention.

The invention claimed is:

1. A lens case, having a longitudinal axis (X), for accommodating an intraocular lens, IOL, (1) having an optical part (1a) and at least two haptics (2) distributed around the optical part (1a), the IOL (1) comprising a central zone (CZ) having a third width (18') perpendicular to the longitudinal axis (X) and two side zones (SZ) each comprising at least one haptic (2) and the two side zones each having a fourth width (17') perpendicular to the longitudinal axis (X), the fourth width (17') being greater than the third width (18'), the lens case (50, 150) comprising a lens case body (3, 103) and a sliding element (4, 104), a sliding connection being provided there between for sliding the sliding element (4, 104) on the lens case body (3, 103) along the longitudinal axis (X) from a first position to a second position;

the lens case body (3, 103) comprising a longitudinal recess (32, 132), having a first part (32a, 132a) and a second part (32b, 132b), the first part (32a, 132a) having a first width (17) perpendicular to the longitudinal axis (X) greater than the fourth width (17'), the second part (32b, 132b) terminating in a loading port (34, 134) and having a second width (18) perpendicular to the longitudinal axis (X) being greater than the third width (18') but smaller than the fourth width (17'); in the first position of the sliding element (4, 104) the IOL (1) being arranged in the recess (32, 132) such that the central zone (CZ) is received in the second part (32b, 132b), a first one of the side zones (SZ) is received in the first part (32a, 132a) and a second one of the side zones (SZ) extends from the recess (32, 132) through the loading port (34, 134); and in the second position of the sliding element (4, 104) the IOL (1) being arranged in the recess (32, 132) such that the second one of the side zones (SZ) is received in the second part (32b, 132b) of the recess (32, 132) in a pre-bent state; the sliding element comprising a bolt (5, 105a) arranged adjacent the loading port (34, 134) for displacing the IOL (1) within the recess (32, 132) along the longitudinal axis (X).

2. The lens case according to claim 1, wherein, a second bolt (105b) is provided on the sliding element (104), which extends into the first part (132a) of the recess.

3. The lens case according to claim 1, wherein, the lens case body (103) comprises an upper portion (103a) and a lower portion (103b) affixed to each other and the recess (132) is provided between the upper portion (103a) and the lower portion (103b).

4. The lens case according to claim 3, wherein, the sliding element (104) is provided with a cantilever hook (144) and the lower portion (103b) of the lens case body (103) is provided with first and second stoppers (118A, 118B) for receiving the hook (144) in the first and second position of the sliding element (104), respectively.

5. The lens case according to claim 1, wherein, the sliding element (4) comprises a cover surface defining an inner space (25) together with the recess (32).

6. The lens case according to claim 5, wherein the lens case body (3) is provided with a lower portion (9) accommodating a rail (6) of a container (7), grooves (10) at its sides and, an upper portion (11) accommodating the IOL (1) in the inner space (25).

7. The lens case according to claim 1, wherein the sliding connection comprises rails (12) on the sliding element (4) and the lens case body (3) comprises corresponding grooves (10).

8. The lens case according to claim 1, wherein the sliding element is a sliding cap (4) and the bolt (5) is provided with a lower portion (13), removably fitted into an opening (14) of the sliding cap (4) and extending to a proximity of a bottom of the recess (32) of the lens case.

9. The lens case according to claim 8, wherein a first stopper (18A) on the groove (10) of the lens case body (3) provides an anchor for the first position of the sliding cap (4), and a second stopper (18B) on the groove (10) of the lens case body (3) provides another anchor for the second position of the sliding cap (4).

10. The lens case according to claim 8, wherein a lower portion (13) of the bolt (5) is provided with a protrusion (19), the width of which is wider than the width of the opening (14) in the sliding cap (4).

11. The lens case according to claim 5, wherein an edge (26) of the sliding cap (4) abuts a collar (27) of the lens case body (3) in the second position of the sliding cap (4).

12. A lens delivery system comprising a lens case (50, 150) according to claim 1 and a container (7, 107) for receiving the lens case (50, 150) therein.

13. The lens delivery system according to claim 12 wherein the sliding element (104) of the lens case (150) comprises sidewardly projecting resilient winglets (143) and a wall (172) of the container (107) is provided with recesses (171) for receiving and retaining the winglets (143) therein in the first position of the sliding element (104), the recesses (171) being dimensioned to release the winglets (143) in the second position of the sliding element (104).

14. The lens delivery system according to claim 13, wherein the sliding element (104) is provided with a cantilever hook (144) and the lens case body (103) is provided with first and second openings (118A, 118B) for receiving the hook (144) in the first and second position of the sliding element (104), respectively.

15. The lens delivery system according to claim 12, further comprising an injector having a cartridge (180) and a lens case receiving part (162) provided with a first protrusion (164A) and a second protrusion (164B) fitting into the first and second openings (118A, 118B), the cartridge (180) having a lens receiving channel (181) a fifth width thereof corresponding to the second width (18) of the second part (132b) of the recess (132) of the lens case body (103) and being level with the recess (132) when the lens case (150) is received in the lens case receiving part (162) of the injector (170), a second sliding connection being provided between the cartridge (180) and the sliding element (104) for sliding the sliding element (104) from the lens case body (103) over the cartridge (180) to an end position in which the sliding element (104) is removable from the cartridge (180).

16. The lens delivery system according to claim 12 wherein the container (7) is provided with a pair of rails (6), a lower portion (9) of the lens case body (3) being provided with corresponding grooves for receiving the rails (6), the rails (6) terminating in resilient bumpers (21) for retaining the lens case body (3) in the first position of the sliding element (4) but releasing the sliding element (4) upon a pulling force.

17. A lens case having a longitudinal axis (X) and comprising a lens case body (3) and a sliding element, the lens case body (3) and the sliding element being provided with first and second guides (10, 12), respectively, for sliding the sliding element on the lens case body (3) along the longitudinal axis (X) from a first position to a second position;
the lens case body (3) comprising a longitudinal recess (32), having a first part (32a) and a second part (32b), the second part (32b) having a second width (18) greater than 4 mm and smaller than 8 mm, the second part (32b) communicating with a loading port (34), the first part (32a) having a first width (17) greater than said second width (18);
the sliding element comprising a bolt (5, 105) arranged adjacent the loading port (34), the bolt being outside of the recess (32) in the first position of the sliding element and extending into the second part (32b) of the recess (32) in the second position of the sliding element.

18. The lens case according to claim 17, further comprising an intraocular lens, IOL, (1) having an optical part (1a) and at least two haptics (2) distributed around the optical part (1a), the IOL (1) consisting of a central zone (CZ) having a third width (18') perpendicular to the longitudinal axis (X) and two side zones (SZ) each comprising at least one haptic (2) and having a fourth width (17') perpendicular to the longitudinal axis (X) greater than the third width (18'), the first width (17) of the first part (32a) of the recess (32) being greater than the fourth width (17') and the second width (18) of the second part (32*b*) of the recess (32) being greater than the third width (18') but smaller than the fourth width (17'), and in the first position of the sliding element the central zone (CZ) being arranged in the second part (32*b*) of the recess (32) such that a first one of the side zones (SZ) is received by the first part (32*a*) of the recess (32) and a second one of the side zones (SZ) extends from the recess (32) through the loading port (34).

19. The lens case according to claim 17, wherein the second width (18) is greater than 6 mm and smaller than 7 mm.

* * * * *